United States Patent
Hisano et al.

(10) Patent No.: US 10,544,084 B2
(45) Date of Patent: Jan. 28, 2020

(54) METHOD FOR PRODUCING 2,6-NAPHTHALENE DICARBOXYLIC ACID

(71) Applicant: UENO FINE CHEMICALS INDUSTRY, LTD., Osaka-shi, Osaka (JP)

(72) Inventors: Takaya Hisano, Takarazuka (JP); Masaki Hamaguchi, Kobe (JP); Yusuke Kita, Yokkaichi (JP); Ryota Motooka, Kobe (JP); Chiaki Terao, Sanda (JP)

(73) Assignee: UENO FINE CHEMICALS INDUSTRY, LTD., Osaka (JP)

( * ) Notice: Subject to any disclaimer, the term of this patent is extended or adjusted under 35 U.S.C. 154(b) by 0 days.

(21) Appl. No.: 16/174,977

(22) Filed: Oct. 30, 2018

(65) Prior Publication Data

US 2019/0127310 A1 May 2, 2019

(30) Foreign Application Priority Data

Oct. 31, 2017 (JP) .................................. 2017-211066

(51) Int. Cl.
| | | |
|---|---|---|
| *C07C 63/00* | (2006.01) | |
| *C07C 51/00* | (2006.01) | |
| *C07C 63/38* | (2006.01) | |
| *C07C 51/47* | (2006.01) | |
| *C07C 51/09* | (2006.01) | |
| *C07C 51/487* | (2006.01) | |

(52) U.S. Cl.
CPC .............. *C07C 63/38* (2013.01); *C07C 51/09* (2013.01); *C07C 51/47* (2013.01); *C07C 51/487* (2013.01)

(58) Field of Classification Search
CPC .......... C07C 63/38; C07C 51/09; C07C 51/47
See application file for complete search history.

(56) References Cited

U.S. PATENT DOCUMENTS

| 2004/0260052 A1 | 12/2004 | Nagao et al. |
| 2005/0240056 A1 | 10/2005 | Kitayama et al. |

FOREIGN PATENT DOCUMENTS

| JP | 3-240750 A | 10/1991 |
| JP | 6-505512 A | 6/1994 |
| JP | 6-256256 A | 9/1994 |
| JP | 2005-272423 A | 10/2005 |
| JP | 2005-272424 A | 10/2005 |
| JP | 2005-272425 A | 10/2005 |
| JP | 2010-168325 A | 8/2010 |
| WO | 93/12065 A1 | 6/1993 |
| WO | 01/16083 A2 | 3/2001 |

OTHER PUBLICATIONS

Extended European Search Report dated Mar. 14, 2019 from the European Patent Office in counterpart European Patent Application No. 18202094.1.

*Primary Examiner* — Sikarl A Witherspoon
(74) *Attorney, Agent, or Firm* — Sughrue Mion, PLLC

(57) ABSTRACT

An object of the present invention is to provide a method for producing high-purity 2,6-NDA having a small alkali metal content. The present invention relates to a method for producing a high-purity 2,6-naphthalene dicarboxylic acid, comprising a purification step of washing a crude 2,6-naphthalene dicarboxylic acid having a specific surface area of 2 m²/g or more in the presence of an aqueous medium under a temperature condition of 90° C. or more and less than 200° C.

17 Claims, No Drawings

METHOD FOR PRODUCING 2,6-NAPHTHALENE DICARBOXYLIC ACID

BACKGROUND OF THE INVENTION

1. Field of the Invention

This patent application claims priority under the Paris Convention based on Japanese Patent Application No. 2017-211066 (filed Oct. 31, 2017), which is incorporated herein by reference in their entirety.

The present invention relates to a method for producing 2,6-naphthalene dicarboxylic acid.

2. Description of the Related Art

As a monomer for producing various polymers such as polyethylene naphthalate, liquid-crystalline polyester, and polyamide, 2,6-naphthalene dicarboxylic acid (hereinafter also referred to as 2,6-NDA) is an important compound. Di-lower alkyl ester such as dimethyl ester of 2,6-naphthalene dicarboxylic acid (hereinafter, di-lower alkyl ester of 2,6-naphthalene dicarboxylic acid is also referred to as 2,6-NDC) is widely used as a monomer for producing various polymers in the same way as 2,6-NDA because of physical properties such as a melting point and ease of use as a monomer.

A conventionally known production method of 2,6-NDA is a method of oxidizing naphthalene having the 2,6-positions substituted with an alkyl group and/or an acyl group by using heavy metal such as cobalt and manganese as a catalyst at the alkyl group and/or the acyl group with molecular oxygen. However, crude 2,6-NDA obtained by this method contains impurities such as an aldehyde type intermediate and an oxidized polymer and therefore cannot directly be used as a monomer for producing a polymer.

Therefore, various purification methods are under study for crude 2,6-NDA obtained by the method described above.

For example, in a generally known method, crude 2,6-NDA is esterified with lower alcohol such as methanol to obtain 2,6-NDC, and subsequently, purification of 2,6-NDC through distillation, recrystallization, etc. is followed by decomposition of an ester group for obtaining high-purity 2,6-NDA.

Regarding the method for producing high-purity 2,6-NDA through decomposition of an ester group of 2,6-NDC described above, proposed methods include a method of decomposing an ester group with an acid catalyst, a method of decomposing an ester group with water under a specific condition, and a method of decomposing an ester group with a basic catalyst.

A known method of decomposing an ester group with an acid catalyst is a method of decomposing the ester group of 2,6-NDC in the presence of an acid catalyst and an aliphatic carboxylic acid to obtain high-purity 2,6-NDA (Japanese Laid-Open Patent Publication No. 6-256256). However, this method requires a long time for reaction and has a problem that aliphatic carboxylic acid esters are generated as by-products at an ester-group decomposition step.

A known method of decomposing an ester group with water under a specific condition is a method of hydrolyzing the ester group of 2,6-NDC at a reaction temperature of at least 450° F. (232° C.) in the presence of an amount of water sufficient for solubilizing at least about 10% of 2,6-NDA generated at a reaction temperature under a liquid phase condition (Japanese Unexamined Patent Application Publication (Translation of PCT Application) No. 6-505512). However, this method requires a very high temperature of 450° F. or more, accordingly requires a very high pressure etc., and is therefore difficult to industrially implement.

Known methods of decomposing an ester group with a basic catalyst are methods of decomposing the ester group with a basic compound by using water and/or an organic solvent to obtain a solution of salt of 2,6-NDA and recovering 2,6-NDA through acid precipitation (Japanese Laid-Open Patent Publication Nos. 3-240750, 2005-272423, 2005-272424, and 2005-272425).

However, in these methods, the obtained 2,6-NDA contains an extremely large amount of alkali metal such as sodium and potassium, so that when used as a raw material for a polymer material such as polyester, the 2,6-NDA causes a problem that the catalysis of the alkali metal makes it difficult to control a behavior of a polymerization reaction and physical properties of an obtained polymer material and a problem that very fine crystals precipitated at the time of acid precipitation makes it difficult to recover 2,6-NDA from slurry after acid precipitation.

Therefore, in a proposed method for producing 2,6-NDA having a small alkali metal content, after decomposing the ester group of 2,6-NDC with a basic catalyst, alcohol in a solution is distilled away (Japanese Laid-Open Patent Publication No. 2010-168325). However, even the 2,6-NDA obtained by this method has the alkali metal content of 40 ppm or more, which may cause the problem described above.

PRIOR ART DOCUMENTS

Patent Document 1: Japanese Laid-Open Patent Publication No. 6-256256
Patent Document 2: Japanese Unexamined Patent Application Publication (Translation of PCT Application) No. 6-505512
Patent Document 3: Japanese Laid-Open Patent Publication No. 3-240750
Patent Document 4: Japanese Laid-Open Patent Publication No. 2005-272423
Patent Document 5: Japanese Laid-Open Patent Publication No. 2005-272424
Patent Document 6: Japanese Laid-Open Patent Publication No. 2005-272425
Patent Document 7: Japanese Laid-Open Patent Publication No. 2010-168325

BRIEF SUMMARY OF THE INVENTION

An object of the present invention is to provide a method for producing high-purity 2,6-NDA having a small alkali metal content.

As a result of intensive studies on the method for producing 2,6-NDA, the inventors found that high-purity 2,6-NDA having a small alkali metal content can easily prepared by washing crystals of 2,6-NDA having a certain specific surface area with an aqueous medium under a high temperature condition, thereby completing the present invention.

Therefore, the present invention provides a method for producing a high-purity 2,6-naphthalene dicarboxylic acid (also referred to as purified 2,6-naphthalene dicarboxylic acid) having an alkali metal content less than 40 ppm comprising a step of washing a crude 2,6-naphthalene dicarboxylic acid (also referred to as unpurified 2,6-naphthalene dicarboxylic acid) having a specific surface area of 2 $m^2/g$ or more in the presence of an aqueous medium under a temperature condition of 90° C. or more and less than 200° C.

According to the method of the present invention, high-purity 2,6-NDA having a small alkali metal content can be produced.

DETAILED DESCRIPTION OF THE INVENTION

A method of obtaining crystals of crude 2,6-NDA having a specific surface area of 2 m$^2$/g or more used in the step (hereinafter also referred to as a purification step) of the present invention is not particularly limited and, for example, the crystals can be obtained by hydrolysis of 2,6-NDC and acid precipitation of an obtained 2,6-NDA alkali metal salt.

In the present invention, crude 2,6-NDA means 2,6-NDA having an alkali metal content of 40 ppm or more, and high purity 2,6-NDA means 2,6-NDA having an alkali metal content less than 40 ppm.

Specific examples of 2,6-NDC include one or more compounds selected from the group consisting of 2,6-naphthalene dicarboxylic acid dimethyl ester, 2,6-naphthalene dicarboxylic acid diethyl ester, 2,6-naphthalene dicarboxylic acid di-n-propyl ester, 2,6-naphthalene dicarboxylic acid di-iso-propyl ester, 2,6-naphthalene dicarboxylic acid di-n-butyl ester, 2,6-naphthalene dicarboxylic acid di-iso-butyl ester, 2,6-naphthalene dicarboxylic acid di-n-pentyl ester, and 2,6-naphthalene dicarboxylic acid di-n-hexyl ester. Among these 2,6-NDCs, 2,6-naphthalene dicarboxylic acid dimethyl ester is particularly preferable because of easy availability etc.

Hydrolysis of 2,6-NDC is usually performed by reacting 2,6-NDC with a basic alkali metal compound in the presence of a solvent.

Examples of the solvent used for reacting 2,6-NDC with a basic alkali metal compound include water or an aqueous solvent selected from mixed solvents of water and alcohol having 1 to 6 carbon atoms. Preferably, water or an alcohol aqueous solution containing alcohol having 1 to 6 carbon atoms in an amount of 10 mass % or less is used as the aqueous solvent.

Specific examples of the alcohol having 1 to 6 carbon atoms include one or more selected from the group consisting of methanol, ethanol, n-propyl alcohol, iso-propyl alcohol, n-butyl alcohol, iso-butyl alcohol, n-pentyl alcohol, and n-hexyl alcohol.

Among these alcohols having 1 to 6 carbon atoms, methanol is preferably used alone because of being easily dissolved in water and easily and inexpensively available.

An amount of the solvent to be used in the present invention is not particularly limited as long as the reaction of 2,6-NDC with the basic alkali metal compound favorably progresses and is preferably 3 to 10 times by mass, more preferably 4 to 8 times by mass, particularly preferably 5 to 7 times by mass based on the mass of 2,6-NDC. When the solvent is less than 3 times by mass, stirring of a reaction solution tends to be difficult, and when the solvent is more than 10 times by mass, a reaction time tends to become long.

In the present invention, examples of the basic alkali metal compound used for decomposing the ester group of 2,6-NDC include one or more selected from the group consisting of sodium hydroxide, potassium hydroxide, sodium carbonate, potassium carbonate, sodium hydrogen carbonate, and potassium hydrogen carbonate.

Among these basic alkali metal compounds, sodium hydroxide or potassium hydroxide is preferably used because of reactivity and being easily and inexpensively available.

When charged into a reaction system, the basic alkali metal compound may be solid or may be dissolved in water or an aqueous solution of alcohol having 1 to 6 carbon atoms into a form of solution.

An amount of the basic alkali metal compound to be used is preferably from 1.0 to 5.0 equivalents, more preferably from 1.0 to 2.0 equivalents, based on the ester group of the 2,6-NDC.

The temperature of reaction of 2,6-NDC with the basic alkali metal compound is not particularly limited as long as the reaction favorably proceeds and is preferably 40 to 200° C., more preferably 60 to 150° C., particularly preferably 80 to 120° C. When the reaction temperature exceeds the boiling point of the solvent, a pressure resistant apparatus may be used for the reaction.

The reaction between 2,6-NDC and the basic alkali metal compound may be performed in air or under an inert gas atmosphere and is preferably performed under an inert gas atmosphere of nitrogen, helium, etc.

Although depending on a kind and an amount of the solvent to be used, the reaction time between 2,6-NDC and the basic alkali metal compound is typically 1 to 50 hours, preferably 2 to 20 hours, more preferably 3 to 10 hours.

A means of confirming the completion of the reaction between 2,6-NDC and the basic alkali metal compound is not particularly limited and can be confirmed, for example, by analyzing a reaction solution with high performance liquid chromatography.

The reaction between 2,6-NDC and the basic alkali metal compound is suitably performed until 95 mol % or more, preferably 98 mol % or more, more preferably 99 mol % or more of the charged 2,6-NDC is converted to a dialkali metal salt of 2,6-NDA.

A solution containing the dialkali metal salt of 2,6-NDA obtained from the reaction between 2,6-NDC and the basic alkali metal compound is then subjected to an acid precipitation step.

The solution containing the dialkali metal salt of 2,6-NDA before acid precipitation may be subjected as needed to a filtration treatment for removing insoluble foreign materials and an adsorbent treatment using activated carbon etc. for removing coloring substances, metals etc.

The step of acid precipitation of the solution containing the dialkali metal salt of 2,6-NDA may be performed in the same reaction tank continuously from the step of reacting 2,6-NDC with the basic alkali metal compound or may be performed after transferring the solution containing the dialkali metal salt of 2,6-NDA to a separately prepared reaction tank.

An acid used at the acid precipitation step is not particularly limited and is preferably a mineral acid. Examples of the mineral acid include binary acids such as hydrochloric acid and hydrofluoric acid, and oxo acids such as sulfuric acid, nitric acid, phosphoric acid, and perchloric acid. Organic acids such as acetic acid and propionic acid are also usable. An amount of these acids to be used is preferably 1.0 to 2.0 equivalents, more preferably 1.1 to 1.5 equivalents, particularly preferably 1.1 to 1.2 equivalents, based on the dialkali metal salt of 2,6-NDA.

Usually, the acid at the acid precipitation step is preferably dropped as an aqueous solution at a constant rate to an aqueous solution containing the dialkali metal salt of 2,6-NDA.

The temperature during acid precipitation is preferably 30 to 95° C., more preferably 50 to 90° C. If the temperature during acid precipitation is less than 30° C., particles of the obtained 2,6-NDA crystals become finer and may clog the filter at the time of filtration. If the temperature during acid precipitation exceeds 95° C., the obtained 2,6-NDA crystals have a small specific surface area and may make it difficult to remove the alkali metal from inside the crystals even when washed with a solvent etc.

The acid precipitation time is preferably 30 to 55 minutes, more preferably 35 to 50 minutes. If the acid precipitation time is less than 30 minutes, a rapid temperature change may occur due to reaction heat. If the acid precipitation time exceeds 55 minutes, the obtained 2,6-NDA crystals have a small specific surface area and may make it difficult to remove the alkali metal from inside the crystals even when washed with a solvent etc.

The acid precipitation may be performed in air or under an inert gas atmosphere and is preferably performed under an inert gas atmosphere of nitrogen, helium, etc.

A slurry of 2,6-NDA obtained by the acid precipitation is subjected to a conventional method such as centrifugal separation, filtration by a filter press, etc. to separate and recover 2,6-NDA from the slurry. Separated 2,6-NDA crystals are washed with cold water, warm water, etc. as needed and then dried.

The 2,6-NDA crystals obtained in this way are subjected to a purification step.

In a production method of the present invention, the purification step is performed by washing crystals of crude 2,6-naphthalene dicarboxylic acid having a specific surface area of 2 $m^2/g$ or more in the presence of an aqueous medium under a temperature condition of 90° C. or more and less than 200° C.

The specific surface area is measured by a gas adsorption method and the specific surface area of the crude 2,6-naphthalene dicarboxylic acid crystals to be subjected to the purification step is 2 $m^2/g$ or more, more preferably 4 $m^2/g$ or more, particularly preferably 5.5 $m^2/g$ or more. If the specific surface area of the 2,6-naphthalene dicarboxylic acid crystals is less than 2 $m^2/g$, an effect of removing the alkali metal decreases. The specific surface area of the crude 2,6-naphthalene dicarboxylic acid is preferably 10 $m^2/g$ or less because of excellent filterability and handling properties.

The specific surface area of the crude 2,6-naphthalene dicarboxylic acid crystals to be subjected to the purification step is 2 $m^2/g$ or more and may be obtained by, for example, pulverizing 2,6-naphthalene dicarboxylic acid crystals having a specific surface area less than 2 $m^2/g$ by using a pulverizer such as a ball mill or may be obtained through crystallization.

If the temperature at the purification step is lower than 90° C., the effect of removing the alkali metal decreases. If the temperature at the purification step is 200° C. or higher, a pressure becomes extremely high in an apparatus, which may cause breakage or rupture of the apparatus.

The purification step is preferably performed in a closed system. A preferred closed-system apparatus used at the purification step is a heat-resistant and pressure-resistant apparatus such as an autoclave and preferably has a stirring apparatus therein.

A pressure in a purification apparatus at the purification step is preferably 1.5 MPa or less, more preferably 1.0 MPa or less. The pressure inside the purification apparatus exceeding 1.5 MPa may cause breakage or rupture of the apparatus.

The aqueous medium used for washing at the purification step is preferably water or an aqueous solution of a water-soluble organic solvent having a concentration up to 20 mass %, and is preferably water.

The water-soluble organic solvent usable in the present invention is preferably a solvent dissolving in water up to 20 mass % at 25° C., and examples of such a solvent include alcoholic solvents such as methanol, ethanol, isopropanol, 2-methoxyethanol, 2-ethoxyethanol, ethylene glycol, glycerin, and polyethylene glycol (e.g., PEG200), ketone solvents such as acetone, aprotic polar solvents such as N,N-dimethylacetamide, N,N-dimethylformamide, dimethyl sulfoxide, hexamethylphosphoramide, and N-methyl-2-pyrrolidone. Two or more of these water-soluble organic solvents may be used in combination.

An amount of the aqueous medium to be used is preferably 200 to 2,000 parts by mass based on 100 parts by mass of 2,6-NDA. If the amount of the aqueous medium to be used is less than 200 parts by mass based on 100 parts by mass of 2,6-NDA, the effect of removing the alkali metal may decrease. If the amount of the aqueous medium to be used exceeds 2000 parts by mass based on 100 parts by mass of 2,6-NDA, a production efficiency may be lowered due to an excessive amount of the wasted aqueous medium etc.

A washing time at the purification step is preferably 10 to 110 minutes, more preferably 40 to 80 minutes. If the washing time is less than 10 minutes, the effect of removing the alkali metal from 2,6-NDA crystals may decreases. If the washing time exceeds 110 minutes, a production efficiency may be lowered.

A slurry of 2,6-NDA obtained at the purification step is subjected to a conventional method such as centrifugal separation, filtration by a filter press, etc. to separate and recover 2,6-NDA from the slurry. Separated 2,6-NDA crystals are washed with cold water, warm water, etc. as needed and then dried.

The high-purity 2,6-NDA obtained in this way is suitably used as a raw material for preparing various chemical products and is particularly suitably used as a monomer for producing liquid-crystalline polyester, polyethylene naphthalate, polyamide, etc. due to a small alkali metal content and high purity.

The alkali metal content contained in the high-purity 2,6-NDA obtained by the method of the present invention is less than 40 ppm, preferably less than 30 ppm, more preferably less than 20 ppm, further preferably less than 10 ppm. Such alkali metal may be present as hydrochloride, sulfate, nitrate, phosphate, etc.

Examples of the alkali metal include sodium and/or potassium.

The upper limit of the specific surface area of the high-purity 2,6-NDA is preferably less than 2 $m^2/g$, more preferably 1.8 $m^2/g$ or less, further preferably 1.6 $m^2/g$ or less, particularly preferably 1.4 $m^2/g$ or less. The lower limit of the specific surface area is preferably 0.01 $m^2/g$ or more.

As described above, the present invention provides 2,6-naphthalene dicarboxylic acid having an alkali metal content less than 40 ppm, preferably less than 30 ppm, more preferably less than 20 ppm, further preferably less than 10 ppm. Examples of the alkali metal include sodium and/or potassium. The upper limit of the specific surface area of such 2,6-naphthalene dicarboxylic acid is preferably less than 2 $m^2/g$, more preferably 1.8 $m^2/g$ or less, further preferably 1.6 $m^2/g$ or less, particularly preferably 1.4 $m^2/g$ or less. The lower limit of the specific surface area is preferably 0.01 m²/g or more.

EXAMPLES

The present invention will hereinafter be described in detail with examples; however, these examples are not intended to limit the scope of the present invention. Physical properties were measured as follows.
[Specific Surface Area]
The specific surface area was measured by a gas adsorption method (nitrogen-adsorption BET-equation single-point method). A surface analyzer (trade name: MONOSORB, manufactured by QUANTA CHLROME) was used as an analyzer, and a mixed gas of 30% nitrogen and 70% helium was used as a carrier gas with liquid nitrogen used as a refrigerant.

Reference Example 1

Into a 1 L flask equipped with a stirrer, a reflux cooling tube, and a thermometer, 122.1 g of 2,6-naphthalene dicarboxylic acid dimethyl ester, 696.1 g of a 1 mass % methanol aqueous solution, and 85.4 g of a 48% NaOH aqueous solution were charged and heated to 90° C. with stirring. The same temperature was maintained for 8 hours to obtain a sodium 2,6-naphthalenedicarboxylate aqueous solution was obtained.
After this aqueous solution was cooled to 50° C. and a slightly remaining raw material (insoluble matter) was filtered off, the mother liquor was transferred to a 2 L flask, and 317.5 g of water was added. This aqueous solution was heated to 90° C. with stirring at 250 rpm, and 78.9 g of 62.5% sulfuric acid was dropped to the aqueous solution over 45 minutes while maintaining the same temperature. The obtained slurry liquid of 2,6-naphthalene dicarboxylic acid was cooled to 50° C., then subjected to solid-liquid separation, and subsequently washed with 1221 g of water.
The obtained solid was dried by an air dryer at 80° C. to obtain 53.4 g of 2,6-NDA crystals (98.8% yield). The alkali metals (Na, K) contained in the 2,6-NDA crystals were measured by inductively coupled plasma (ICP) emission spectroscopy, and the specific surface area was measured by the gas adsorption method. The results are shown in Table 1.

Example 1

In a 1 L autoclave, 25 g of the 2,6-NDA crystals obtained in Reference Example 1 and 500 g of water (20 times by mass based on NDA) were placed and sealed. The slurry liquid was heated to 140° C. and then washed at 0.3 MPa for 1 hour with stirring. After washing, the slurry liquid was cooled to 70° C. and then subjected to solid-liquid separation. The obtained solid was dried by an air dryer at 80° C. to obtain 24.7 g of 2,6-NDA crystals (98.8% yield). The alkali metals (Na, K) contained in the 2,6-NDA crystals were measured by inductively coupled plasma (ICP) emission spectroscopy, and the specific surface area was measured by the gas adsorption method. The results are shown in Table 1.

Reference Example 2

As in Reference Example 1 except that the temperature during dripping of 62.5% sulfuric acid to the aqueous solution was changed to 70° C., 53.6 g of 2,6-NDA crystals were obtained (99.2% yield). The alkali metals (Na, K) contained in the 2,6-NDA crystals were measured by inductively coupled plasma (ICP) emission spectroscopy, and the specific surface area was measured by the gas adsorption method. The results are shown in Table 1.

Example 2

As in Example 1 except that 2,6-NDA used in washing at the purification step was changed to that obtained in Reference Example 2, 24 g of 2,6-NDA crystals were obtained (98.4% yield). The alkali metals (Na, K) contained in the 2,6-NDA crystals were measured by inductively coupled plasma (ICP) emission spectroscopy, and the specific surface area was measured by the gas adsorption method. The results are shown in Table 1.

Reference Example 3

As in Reference Example 1 except that the temperature during dripping of 62.5% sulfuric acid to the aqueous solution was changed to 50° C., 104.2 g of 2,6-NDA crystals were obtained (96.4% yield). The alkali metals (Na, K) contained in the 2,6-NDA crystals were measured by inductively coupled plasma (ICP) emission spectroscopy, and the specific surface area was measured by the gas adsorption method. The results are shown in Table 1.

Example 3

As in Example 1 except that 2,6-NDA used in washing was changed to that obtained in Reference Example 3, 24.6 g of 2,6-NDA crystals were obtained (98.4% yield). The alkali metals (Na, K) contained in the 2,6-NDA crystals were measured by inductively coupled plasma (ICP) emission spectroscopy, and the specific surface area was measured by the gas adsorption method. The results are shown in Table 1.

Reference Example 4

As in Reference Example 1 except that the dropping time of 62.5% sulfuric acid to the aqueous solution was changed to 60 minutes, 102.1 g of 2,6-NDA crystals were obtained (94.5% yield). The alkali metals (Na, K) contained in the 2,6-NDA crystals were measured by inductively coupled plasma (ICP) emission spectroscopy, and the specific surface area was measured by the gas adsorption method. The results are shown in Table 1.

Comparative Example 1

As in Example 1 except that 2,6-NDA used in washing was changed to that obtained in Reference Example 4, 24.3 g of 2,6-NDA crystals were obtained (97.2% yield). The alkali metals (Na, K) contained in the 2,6-NDA crystals were measured by inductively coupled plasma (ICP) emission spectroscopy, and the specific surface area was measured by the gas adsorption method. The results are shown in Table 1.

Reference Example 5

In a table-top ball mill, 30 g of 2,6-NDA crystals obtained as in Reference Example 4 were placed and pulverized for 12 hours. The specific surface area of the pulverized 2,6-

NDA crystals was measured by the gas adsorption method. The results are shown in Table 1.

Example 4

As in Example 1 except that 2,6-NDA used in washing was changed to that obtained in Reference Example 5, 24.6 g of 2,6-NDA crystals were obtained (98.4% yield). The alkali metals (Na, K) contained in the 2,6-NDA crystals were measured by inductively coupled plasma (ICP) emission spectroscopy, and the specific surface area was measured by the gas adsorption method. The results are shown in Table 1.

Reference Example 6

As in Reference Example 1 except that the dropping time of 62.5% sulfuric acid to the aqueous solution was changed to 48 minutes, 106.5 g of 2,6-NDA crystals were obtained (98.5% yield). The alkali metals (Na, K) contained in the 2,6-NDA crystals were measured by inductively coupled plasma (ICP) emission spectroscopy, and the specific surface area was measured by the gas adsorption method. The results are shown in Table 1.

Example 5

As in Example 1 except that 2,6-NDA used in washing was changed to that obtained in Reference Example 6 and that the amount of water used for washing was changed to 500 g (10 times by mass based on NDA), 49.6 g of 2,6-NDA crystals were obtained (99.1% yield). The alkali metals (Na, K) contained in the 2,6-NDA crystals were measured by inductively coupled plasma (ICP) emission spectroscopy, and the specific surface area was measured by the gas adsorption method. The results are shown in Table 1.

Example 6

As in Example 5 except that except that the amount of 2,6-NDA crystals used for washing was changed to 100 g, 99.1 g of 2,6-NDA crystals were obtained (99.1% yield). The alkali metals (Na, K) contained in the 2,6-NDA crystals were measured by inductively coupled plasma (ICP) emission spectroscopy, and the specific surface area was measured by the gas adsorption method. The results are shown in Table 1.

Reference Example 7

As in Reference Example 1 except that 85.4 g of a 48% NaOH aqueous solution was changed to 119.8 g of a 48% KOH aqueous solution, 104.1 g of 2,6-NDA crystals were obtained (96.3% yield). The alkali metals (Na, K) contained in the 2,6-NDA crystals were measured by inductively coupled plasma (ICP) emission spectroscopy, and the specific surface area was measured by the gas adsorption method. The results are shown in Table 1.

Example 7

As in Example 1 except that 2,6-NDA used in washing was changed to that obtained in Reference Example 7, 24.1 g of 2,6-NDA crystals were obtained (98.2% yield). The alkali metals (Na, K) contained in the 2,6-NDA crystals were measured by inductively coupled plasma (ICP) emission spectroscopy, and the specific surface area was measured by the gas adsorption method. The results are shown in Table 1.

Example 8

As in Example 7 except that the temperature during washing was changed to 95° C., 24.7 g of 2,6-NDA crystals were obtained (98.7% yield). The alkali metals (Na, K) contained in the 2,6-NDA crystals were measured by inductively coupled plasma (ICP) emission spectroscopy, and the specific surface area was measured by the gas adsorption method. The results are shown in Table 1.

Example 9

As in Example 7 except that the temperature during washing was changed to 180° C., 24.2 g of 2,6-NDA crystals were obtained (96.9% yield). The alkali metals (Na, K) contained in the 2,6-NDA crystals were measured by inductively coupled plasma (ICP) emission spectroscopy, and the specific surface area was measured by the gas adsorption method. The results are shown in Table 1.

Reference Example 8

Into a 1 L flask equipped with a stirrer, a reflux cooling tube, and a thermometer, 108.1 g of 2,6-NDA and 646.2 g of water were charged and heated to 40° C. with stirring. Into this flask, 119.4 g of 48% potassium hydroxide was added and stirred at the same temperature for 30 minutes. After filtering off insoluble matters, the mother liquor was transferred to a 2 L flask, and 59.0 g of methanol and 439.6 g of water were further added and heated to 86° C. with stirring. While maintaining the same temperature, 88.0 g of 62.5% sulfuric acid was dropped to the aqueous solution over 135 minutes. After stirring at the same temperature for 30 minutes, the obtained slurry liquid of 2,6-naphthalene dicarboxylic acid was cooled to 50° C., then subjected to solid-liquid separation, and subsequently washed with 46.7 g of water.

To a 2 L flask, 125.5 g of the obtained solid was transferred, and 1239 g of water was further added and stirred at 25° C. for 1 hour. The obtained slurry liquid of 2,6-naphthalene dicarboxylic acid was subjected to solid-liquid separation and then washed with 23.4 g of water.

The obtained solid was dried by an air dryer at 80° C. to obtain 105.5 g of 2,6-NDA crystals (97.6% yield). The alkali metals (Na, K) contained in the 2,6-NDA crystals were measured by inductively coupled plasma (ICP) emission spectroscopy, and the specific surface area was measured by the gas adsorption method. The results are shown in Table 1.

Comparative Example 2

As in Example 1 except that 2,6-NDA used in washing was changed to that obtained in Reference Example 8 and the temperature during washing to 180° C., 24.5 g of 2,6-NDA crystals were obtained (98.1% yield). The alkali metals (Na, K) contained in the 2,6-NDA crystals were measured by inductively coupled plasma (ICP) emission spectroscopy, and the specific surface area was measured by the gas adsorption method. The results are shown in Table 1.

TABLE 1

| | temperature during dropping of sulfuric acid in manufacturing of crude 2,6-NDA (° C.) | washing condition | | 2,6-NDA crystals | | | |
|---|---|---|---|---|---|---|---|
| | | amount of aqueous medium (times by mass/2,6-NDA) | temperature (° C.) | Na (ppm) | K (ppm) | alkali metal removal rate (%) | specific surface area (m²/g) |
| Reference Example 1 | 90 | — | — | 23.6 | 1.1 | — | 5.87 |
| Example 1 | — | 20 | 140 | 2.6 | 1.1 | 85.0 | 0.75 |
| Reference Example 2 | 70 | — | — | 14.3 | 0.6 | — | 6.44 |
| Example 2 | — | 20 | 140 | 0.8 | 0.4 | 91.9 | 0.46 |
| Reference Example 3 | 50 | — | — | 93.0 | 1.6 | — | 5.77 |
| Example 3 | — | 20 | 140 | 0.8 | 0.3 | 98.8 | 0.58 |
| Reference Example 4 | 90 | — | — | 74.6 | 0.7 | — | 0.47 |
| Comparative Example 1 | — | 20 | 140 | 28.7 | 0.3 | 61.5 | 0.93 |
| Reference Example 5 | — | — | — | 62.0 | 1.1 | — | 2.49 |
| Example 4 | — | 20 | 140 | 5.9 | 2.3 | 87.0 | 0.78 |
| Reference Example 6 | 90 | — | — | 48.0 | 0.7 | — | 5.79 |
| Example 5 | — | 10 | 140 | 0.6 | 0.2 | 98.4 | 0.30 |
| Example 6 | — | 5 | 140 | 0.7 | 0.4 | 97.7 | 0.33 |
| Reference Example 7 | 90 | — | — | 7.0 | 909.2 | — | 4.44 |
| Example 7 | — | 20 | 140 | 0.6 | 6.7 | 99.2 | 0.93 |
| Example 8 | — | 20 | 95 | 1.1 | 19.9 | 97.7 | 1.53 |
| Example 9 | — | 20 | 180 | 0.8 | 5.2 | 99.3 | 0.32 |
| Reference Example 8 | 90 | — | — | 1.3 | 122.1 | — | 0.33 |
| Comparative Example 2 | — | 20 | 180 | 0.9 | 48.1 | 60.3 | 0.33 |

* alkali metal removal rate (%) = [(alkali metal amount before washing − alkali metal amount after washing)/alkali metal amount before washing] × 100

As shown in Table 1, it is understood that by washing 2,6-NDA of Reference Examples 1 to 3, and 5 to 7 having a predetermined specific surface area in the presence of an aqueous medium at a predetermined temperature condition, the contained alkali metals can significantly be removed as compared to the case of washing 2,6-NDA of Reference Examples 4 and 8 having a specific surface area less than the predetermined range (Examples 1 to 9, Comparative Examples 1 to 2).

What is claimed is:

1. A method for producing a high-purity 2,6-naphthalene dicarboxylic acid, comprising:
   a step of washing a crude 2,6-naphthalene dicarboxylic acid having a specific surface area of 2 m²/g or more in the presence of an aqueous medium under a temperature condition of 90° C. or more and less than 200° C., wherein an alkali metal content contained in the high-purity 2,6-naphthalene dicarboxylic acid is less than 20 ppm.

2. The method according to claim 1, wherein the high-purity 2,6-naphthalene dicarboxylic acid has a specific surface area less than 2 m²/g.

3. The method according to claim 1, wherein the washing is performed in the presence of 200 to 2,000 parts by mass of the aqueous medium based on 100 parts by mass of the crude 2,6-naphthalene dicarboxylic acid.

4. The method according to claim 2, wherein the washing is performed in the presence of 200 to 2,000 parts by mass of the aqueous medium based on 100 parts by mass of the crude 2,6-naphthalene dicarboxylic acid.

5. The method according to claim 1, wherein the crude 2,6-naphthalene dicarboxylic acid is obtained by acid precipitation of a 2,6-naphthalene dicarboxylic acid alkali metal salt.

6. The method according to claim 2, wherein the crude 2,6-naphthalene dicarboxylic acid is obtained by acid precipitation of a 2,6-naphthalene dicarboxylic acid alkali metal salt.

7. The method according to claim 3, wherein the crude 2,6-naphthalene dicarboxylic acid is obtained by acid precipitation of a 2,6-naphthalene dicarboxylic acid alkali metal salt.

8. The method according to claim 4, wherein the crude 2,6-naphthalene dicarboxylic acid is obtained by acid precipitation of a 2,6-naphthalene dicarboxylic acid alkali metal salt.

9. The method according to claim 5, wherein the 2,6-naphthalene dicarboxylic acid alkali metal salt is obtained by hydrolyzing 2,6-naphthalene dicarboxylic acid dialkyl ester.

10. The method according to claim 6, wherein the 2,6-naphthalene dicarboxylic acid alkali metal salt is obtained by hydrolyzing 2,6-naphthalene dicarboxylic acid dialkyl ester.

11. The method according to claim 7, wherein the 2,6-naphthalene dicarboxylic acid alkali metal salt is obtained by hydrolyzing 2,6-naphthalene dicarboxylic acid dialkyl ester.

12. The method according to claim 8, wherein the 2,6-naphthalene dicarboxylic acid alkali metal salt is obtained by hydrolyzing 2,6-naphthalene dicarboxylic acid dialkyl ester.

13. The method according to claim 5, wherein the acid precipitation is performed by dropping an acid aqueous solution to an aqueous solution containing a 2,6-naphthalene dicarboxylic acid alkali metal salt for 30 to 55 minutes under a temperature condition of 30 to 95° C.

14. The method according to claim 5, wherein the acid precipitation is performed by dropping an acid aqueous solution to an aqueous solution containing a 2,6-naphthalene dicarboxylic acid alkali metal salt for 30 to 55 minutes under a temperature condition of 30 to 95° C.

15. The method according to claim 10, wherein the acid precipitation is performed by dropping an acid aqueous solution to an aqueous solution containing a 2,6-naphthalene dicarboxylic acid alkali metal salt for 30 to 55 minutes under a temperature condition of 30 to 95° C.

16. A 2,6-naphthalene dicarboxylic acid having an alkali metal content less than 20 ppm and a specific surface area less than 2 $m^2/g$.

17. The 2,6-naphthalene dicarboxylic acid according to claim 16, wherein the alkali metal is sodium and/or potassium.

* * * * *